US011981893B2

(12) United States Patent
Soon-Shiong et al.

(10) Patent No.: US 11,981,893 B2
(45) Date of Patent: May 14, 2024

(54) DNA STABILIZATION OF RNA

(71) Applicant: Nantomics, Culver City, CA (US)

(72) Inventors: Patrick Soon-Shiong, Culver City, CA (US); Shahrooz Rabizadeh, Agoura Hills, CA (US); Kathleen Danenberg, Altadena, CA (US)

(73) Assignee: Nantomics LLC, Culver City, CA (US)

( * ) Notice: Subject to any disclaimer, the term of this patent is extended or adjusted under 35 U.S.C. 154(b) by 152 days.

(21) Appl. No.: 17/493,637

(22) Filed: Oct. 4, 2021

(65) Prior Publication Data

US 2022/0025362 A1    Jan. 27, 2022

Related U.S. Application Data

(62) Division of application No. 16/618,017, filed as application No. PCT/US2018/035123 on May 30, 2018, now Pat. No. 11,168,323.

(60) Provisional application No. 62/513,947, filed on Jun. 1, 2017.

(51) Int. Cl.
*C12N 15/11* (2006.01)
*C12N 15/10* (2006.01)
*C12Q 1/6876* (2018.01)

(52) U.S. Cl.
CPC .......... *C12N 15/11* (2013.01); *C12N 15/1003* (2013.01); *C12Q 1/6876* (2013.01); *C12N 2320/51* (2013.01); *C12Q 2565/00* (2013.01)

(58) Field of Classification Search
CPC ............ C12N 15/1003; C12N 2320/51; C12Q 2565/00
See application file for complete search history.

(56) References Cited

U.S. PATENT DOCUMENTS

| | | | |
|---|---|---|---|
| 6,617,170 B2 | 9/2003 | Augello et al. | |
| 8,304,187 B2 | 11/2012 | Fernando | |
| 8,586,306 B2 | 11/2013 | Fernando | |
| 2008/0131880 A1* | 6/2008 | Bortolin | C12Q 1/6823 703/11 |
| 2010/0028852 A1 | 2/2010 | Lader | |
| 2011/0111410 A1 | 5/2011 | Ryan et al. | |
| 2013/0209997 A1 | 8/2013 | Whitney et al. | |
| 2014/0087366 A1 | 3/2014 | Srinivasan et al. | |
| 2014/0199681 A1 | 7/2014 | Ryan et al. | |
| 2017/0067803 A1 | 3/2017 | Jackson et al. | |
| 2020/0172900 A1 | 6/2020 | Soon-Shiong et al. | |

FOREIGN PATENT DOCUMENTS

| EP | 2 112 232 B1 | 4/2014 |
|---|---|---|
| EP | 3 103 883 A1 | 12/2016 |
| EP | 2 898 069 B1 | 4/2018 |
| WO | 2010/096323 A1 | 8/2010 |
| WO | 2011/057184 A1 | 5/2011 |
| WO | 2013/045457 A1 | 4/2013 |
| WO | 2014/029791 A1 | 2/2014 |
| WO | 2015/140218 A1 | 9/2015 |
| WO | 2016/077709 A1 | 5/2016 |
| WO | 2016/161023 A1 | 10/2016 |
| WO | 2018/222709 A2 | 12/2018 |
| WO | 2018/222709 A3 | 1/2019 |

OTHER PUBLICATIONS

Cherepanova et al , Immunochemical assay for deoxyribonuclease activity in body fluids, Journal of Immunological Methods, 2007, vol. 325, issues 1-2, pp. 96-103 (Year: 2007).*
Hallick et al., "Use of aurintricarboxylic acid as an inhibitor of nucleases during nucleic acid isolation", Nucleic Acids Research, Sep. 1977, vol. 4, No. 9, pp. 3055-3064.
International Search report and Written Opinion received for PCT Application Serial No. PCT/US2018/035123 dated Nov. 16, 2018, 15 pages.
Qin et al., "A novel blood collection device stabilizes cell-free RNA in blood during sample shipping and storage", BMC Research Notes, 2013, vol. 6, 12 pages.
Skidmore et al., "Characterization and use of the potent ribonuclease inhibitor aurintricarboxylic acid for the isolation of RNA from animal tissues", Biochem. J., 1989, vol. 263, pp. 73-80.
Streck, "Blood Collection Tube", Cell-Free RNA BCT, 2017, 1 page.
Tan et al., "DNA, RNA, and Protein Extraction: The Past and the Present", Journal of Biomedicine and Biotechnology, 2009, vol. 2009, 10 pages.
Written Opinion received for PCT Application Serial No. PCT/US2018/035123 dated Jul. 19, 2019, 11 pages.
Kolarevic et al., "Deoxyribonuclease inhibitors", European Journal of Medicinal Chemistry, 2014, 11 pages.
Extended European Search report received for European patent Application Serial No. 18810720.5 dated May 8, 2020, 10 pages.
Qin et al., "Stabilization of circulating tumor cells in blood using a collection device with a preservative reagent", Cancer Cell International, 2014, vol. 14, No. 23, pp. 1-6.
Das et al., "Stabilization of Cellular RNA in Blood During Storage at Room Temperature: A Comparison of Cell-Free RNA BCT(®) With K3EDTA Tubes", Mol Diagn Ther, 2014, 7 pages.
International Preliminary Report on Patentability Chapter II received for PCT/US2018/035123 dated Dec. 27, 2019, 12 pages.
Non-Final Office Action received for U.S. Appl. No. 16/618,017 dated Jan. 8, 2021, 22 pages.
Keller et al., "Degradation of DNA RNA Hybrids by Ribonuclease H and DNA Polymerases of Cellular and Viral Origin", PNAS, 1972, vol. 69, No. 11, 3360-3364.
Final Office Action received for U.S. Appl. No. 16/618,017 dated Apr. 23, 2021, 11 pages.
Yao et al., "Evaluation and comparison of in vitro degradation kinetics of DNA in serum, urine and saliva: A qualitative study", Gene, 2016, vol. 590, pp. 142-148.
Notice of Allowance received for U.S. Appl. No. 16/618,017 dated Aug. 25, 2021, 14 pages.

\* cited by examiner

*Primary Examiner* — Ekaterina Poliakova-Georgantas
(74) *Attorney, Agent, or Firm* — Martin Fessenmaier; Umberg Zipser LLP

(57) ABSTRACT

RNA from a biological fluid is stabilized during isolation and/or storage using DNA. In especially preferred aspects, the RNA is cfRNA and/or ctRNA, and the biological fluid is blood.

12 Claims, No Drawings

DNA STABILIZATION OF RNA

This application claims priority to allowed U.S. application with the Ser. No. 16/618,017, filed Nov. 27, 2019, which claims priority to our U.S. provisional patent application with the Ser. No. 62/513,947, filed Jun. 1, 2017, all of which are incorporated by reference herein.

FIELD OF THE INVENTION

The field of the invention is validation systems and methods for detection of genetic variation, especially as it relates to computational analysis of whole genome data.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cell-free DNA (cfDNA) has been known and characterized from biological fluids for many years, and cfDNA has been employed in certain efforts to diagnose cancer and monitor treatment response of a cancer. More recently, advances in molecular genetics have not only enabled detection of cfDNA at relatively low levels, but have also allowed identification of mutated cfDNA. Due to the convenient manner of obtaining cfDNA, analysis of circulating nucleic acids has become an attractive tool in diagnosis and treatment of cancer. However, cfDNA analysis is somewhat limited in that information obtained does not provide insight about actual translation and potential presence of the corresponding protein.

To circumvent at least some the difficulties associated with cfDNA, compositions and methods for detection and analysis of cell free RNA (cfRNA) have recently been developed, and exemplary methods are described in WO 2016/077709. While detection of cfRNA is desirable from various perspectives, numerous difficulties nevertheless remain. Among other factors, as at least certain tumor specific cfRNA are relatively rare, cfRNA tests need to have significant sensitivity and specificity. Such challenge in the analysis of disease (and especially cancer) is still further compounded by the fact that not all tumors have universal markers (e.g., HER2, PSA, etc.) that can be conveniently monitored via ctRNA. Moreover, cfRNA is unstable in patient blood per se and must therefore be processed within a short period of time. Furthermore, extracted cfRNA is also unstable and is typically stabilized by immediate reverse transcription to the more stable cDNA form.

Certain known processes and compositions use a combination of various ingredients to stabilize cell free RNA in blood samples, as for example, described in U.S. Pat. No. 8,586,306. Here, aurintricaboxylic acid is combined with diazolidinyl urea, glyceraldehyde, sodium fluoride, and EDTA. While at least some of these reagents will reduce RNA degradation, they may interfere with various downstream assays, especially where such assays are quantitative assays such as qPCR.

Thus, there remains a need for compositions and methods to stabilize RNA or increase the yield of RNA, particularly where the RNA is cfRNA or ctRNA that is contained in or that is isolated from a biological fluid.

SUMMARY OF THE INVENTION

The inventive subject matter is directed to compositions and methods of stabilizing RNA, and especially stabilizing cfRNA and ctRNA. Most typically, the RNA is contained in or isolated from a biological fluid (e.g., blood), and exogenous DNA and/or one or more DNAse inhibitors are added to the RNA in an amount effective to stabilize or increase yield of RNA. Such advantages are unexpected as currently known isolation protocols for RNA and especially cfRNA require removal and/or destruction of DNA. Similarly, in addition to or as replacement of exogenous DNA, exogenous RNA may be added (e.g., tRNA, rRNA, miRNA, synthetic RNA, plant RNA, etc.) to stabilize and/or increase yield of cfRNA/ctRNA.

In one aspect of the inventive subject matter, the inventors contemplate a method of stabilizing RNA in an isolated volume of a fluid that includes a step of adding an exogenous DNA and/or a DNAse inhibitor to the fluid. Most typically, the RNA is a cfRNA or a ctRNA. Moreover, it is generally contemplated that such methods may also include a step of adding an RNAse inhibitor to the fluid. With respect to the fluid it is contemplated that the fluid is a biological fluid (e.g., whole blood, serum, plasma, saliva, urine, or ascitic fluid), which may be collected in a blood collection tube.

In some embodiments, the exogenous DNA is human DNA (e.g., from the same human as the RNA that is to be isolated), while in other embodiments the exogenous DNA has a sequence portion that has sequence homology or sequence complementarity of at least 70% with the RNA. Alternatively, the exogenous DNA may also DNA from a non-human organism (i.e., from a species other than the species from which the RNA is to be isolated). Regardless of the source, the exogenous DNA may present in excess (e.g., at least 10-fold molar excess) relative to the RNA that is to be isolated.

Where a DNAse inhibitor is added to the fluid, it is generally preferred that the DNAse inhibitor is present to maintain integrity of at least 90% of the DNA during the isolation process of the RNA or during storage for at least 1 week of the fluid (e.g., at 4° C.). Moreover, it is also contemplated that an RNAse inhibitor may be to the fluid (which is typically distinct from the DNAse inhibitor).

Therefore, in another aspect of the inventive subject matter, the inventors also contemplate a method of collecting cfRNA from blood that includes a step of introducing the blood into a collection tube that contains exogenous DNA. Most typically, but not necessarily, the cfRNA is from a tumor and/or the exogenous DNA is human DNA. With respect to the exogenous DNA, the same considerations as provided above apply. Furthermore, it is contemplated that the collection tubes in such methods may also contain a DNAse inhibitor, and optionally further contain an RNase inhibitor.

Viewed from a different perspective, the inventors therefore also contemplate a method of isolating RNA (and preferably cfRNA) that includes the steps of obtaining a fluid (e.g., whole blood) that contains RNA and genomic DNA, adding exogenous DNA to the fluid to form a mixed nucleic acid solution, and optionally removing cells from the fluid, contacting a solid carrier with the mixed nucleic acid solution to adsorb the RNA onto the solid carrier, and eluting the RNA from the carrier under conditions that separates the eluted RNA from the genomic DNA and exogenous DNA. With respect to the exogenous DNA, the same considerations as provided above apply.

In some embodiments, the solid carrier comprises a silica resin or a DEAE (diethylaminoethyl)-modified resin. Additionally, the step of eluting may include elution with a salt solution having insufficient ionic strength to elute the genomic DNA and exogenous DNA. In other embodiments, such method may also include a step of combining a DNAse inhibitor, and optionally further an RNase inhibitor, with the mixed nucleic acid solution.

Consequently, use of exogenous DNA, and optionally further a DNAse inhibitor, is contemplated to stabilize RNA or increase yield of RNA in an RNA isolation process, wherein the RNA is contained in an isolated volume of a fluid, and wherein the exogenous DNA is added to the fluid.

Various objects, features, aspects and advantages of the inventive subject matter will become more apparent from the following detailed description of preferred embodiments, along with the accompanying drawing figures in which like numerals represent like components.

DETAILED DESCRIPTION

The inventors have previously discovered that cfRNA, and especially ctRNA, can be employed as a sensitive, selective, and quantitative marker for diagnosis, monitoring of treatment, and even as discovery tool that allows repeated and non-invasive sampling of a patient. For example, ctRNA was isolated from whole blood and processed under conditions that preserved cellular integrity. Once separated from the non-nucleic acid components, the circulating nucleic acids were then quantified, typically using real time quantitative PCR and analyzed for a particular disease, disease stage, one or more specific mutations, and/or even personal mutational profiles or presence of expressed neoepitopes. Alternatively, RNAseq could be used to cover at least part of a patient transcriptome, in a single test or over a time course with repeated sampling to obtain a dynamic picture without the need for biopsy of the tumor or a metastasis. However, such analyses were often difficult due to the low abundance of cfRNA and the relatively low stability of cfRNA.

The inventors have now discovered various compositions and methods for stabilizing RNA, and particularly cfRNA that increased yield and stability of RNA, especially where the RNA is isolated from a biological fluid. Most notably, while most of the conventional RNA isolation protocols deem DNA as a contaminant that requires enzymatic removal by DNAseI (see URL:m.youtube.com/watch?v=xaoeA8n4Poo, or WO 2016/161023), the inventors have now recognized that DNA may in fact provide a stabilizing effect to RNA, and especially to ctRNA. In that context, it should be noted that the DNA is exogenous DNA, that is, DNA not originally contained in the sample from which the RNA is to be isolated. For example, such exogenous DNA may be derived from the same patient or may be exogenous DNA that is derived from a non-sample/non-patient origin. Moreover, it should be appreciated that the exogenous DNA (and/or DNA genuine to the sample) may be preserved by addition of a DNAse inhibitor.

Therefore, the inventors particularly contemplate various methods, kits, and uses of exogenous DNA to stabilize RNA (and especially cfRNA) in an isolated volume of a fluid by adding exogenous DNA and/or DNAse inhibitors to the fluid. It is also generally preferred that the fluid is a biological fluid (e.g., blood, serum, plasma, saliva, urine, or ascitic fluid). It should further be appreciated that contemplated compositions and methods will also include one or more RNAse inhibitors (which are typically distinct from the DNAse inhibitors where they are used).

While not wishing to be bound by any particular theory or hypothesis, it is generally contemplated that at least some of the exogenous DNA and the RNA will associate, possibly in a sequence specific manner to form triplex structures, heteroduplex structures, etc., which are suspected to resist DNAse and/or RNase degradation to at least some degree.

Therefore, suitable exogenous DNA may originate from various sources, especially including human origin. For example, the exogenous DNA may be from the same patient or from an allogenic donor (which may or may not be related). However, in other aspects, the exogenous DNA may also be of non-human origin, or more generally, the exogenous DNA may be derived from organism that belongs to a species other than the species from which the RNA is to be isolated. For example, where the RNA to be isolated in human, the exogenous DNA may be plant derived (e.g., using Maxwell® RSC PureFood GMO and Authentication Kit, Promega Corp. USA) or animal based from solid tissues or from blood (e.g., DNeasy Blood & Tissue Kit, Qiagen, USA), or be a commercially available DNA (e.g., RNAse free salmon sperm DNA). Therefore, it should be noted that the exogenous DNA may have a sequence identity or sequence homology that allows target-specific hybridization to so form a heteroduplex, triplex or even higher order complex. Viewed from a different perspective, the exogenous DNA may have sequence homology or sequence complementarity of at least 60%, or at least 70%, or at least 80%, or at least 90% with the RNA that is to be isolated.

In further contemplated aspects, the exogenous DNA will typically be linear double stranded DNA of varying length, and as such may be sheared or genomic DNA. Therefore, the size of the exogenous DNA (or fragments thereof) will typically be at least 1 kBp, or at least 5 kBp, or at least 10 kBp, or at least 20 kBp, or at least 50 kBp. Alternatively, the exogenous DNA may be circular and obtained as plasmid or cosmid DNA or as phage (or other viral type) DNA. Advantageously, such DNA will bear low to no sequence homology to human genes and with that to the RNA to be isolated.

Where the exogenous DNA is from the same organism or species, the ratio of total exogenous DNA to RNA may be between 50:1 and 1:5, or between 10:1 and 1:2, or between 5:1 and 1:1, or between 5:1 and 2:1. Of course, it should be noted that the ratios may be molar ratios or ratios of total base count (exogenous DNA and RNA). Thus, and especially where the association between the exogenous DNA and the RNA is non-specific, the exogenous DNA may be present in molar excess over the RNA (or excess with respect to total base count of exogenous DNA and RNA), such as an at least 2-fold, or an at least 5-fold, or an at least 10-fold, or an at least 50-fold excess relative to the RNA. Viewed from different perspective, suitable quantities of exogenous DNA will include amounts of between 10-100 ng/ml, or between 50-500 ng/ml, or between 100-1,000 ng/ml, or between 500 ng/ml and 2.0 µg/ml, or between 1.0-5.0 µg/ml of the fluid in which the RNA is present (e.g., whole blood, urine, saliva, etc.), and even higher.

Thus, it should be recognized that the exogenous DNA may be added in a non-target specific manner by adding genomic exogenous DNA to the biological fluid, specimen container, tissue, etc. However, where the sequence or sequences of the cfRNA of interest are known, the exogenous DNA may also be target specific. For example, the DNA may be selected to be identical or substantially identical (i.e., at least 98% sequence identity) in sequence relative to the cfRNA to facilitate sequence specific association (e.g., mixed complex, triple helix, etc. Similarly, the exogenous DNA may be substantially larger than the RNA and as such include further DNA sequences in addition to the identical or substantially identical sequences. On the other hand, where background signal or DNA contamination is a concern, the exogenous DNA may be selected to have a sequence that has minimal sequence similarity (i.e., equal or less than 80%, or equal or less than 70%, or equal or less than 60%, or equal or less than 50% sequence identity) relative to the cfRNA. For example, such minimal sequence similarity can be achieved for human RNA where plasmid DNA (e.g., pBR322) is employed. In further contemplated aspects, it should be appreciated that the exogenous DNA may also be supplemented, or replaced at least to some degree, by exogenous RNA, and substantially the same considerations as noted above for exogenous DNA apply for the exogenous RNA. Therefore, suitable exogenous RNA ill include tRNA, rRNA, miRNA, synthetic RNA, plant RNA, etc., as well as mRNA, each of which may originate from the same or different species.

Alternatively, or in addition to use of exogenous DNA, it should be appreciated that one or more DNAse inhibitors may be provided to preserve endogenous and/or exogenous DNA in the sample fluid or collection container. There are numerous DNAse inhibitors known in the art, and all of them are deemed suitable for use herein (see e.g., *Eur J Med Chem.* 2014 Dec. 17; 88:101-11). Furthermore, DNAse inhibitors also include commercially available inhibitors well known in the art. Among others, suitable DNAse inhibitors include 2-mercaptoethanol, 2-nitro-5-thiocyanobenzoic acid, actin, aflatoxin B2a, G2, G2a, and M, or EGTA or EDTA, SDS, calf spleen inhibitor protein, or DNAse inhibitors from Nicotiana tabacum, or carbodiimide and cholesterol sulfate. Further contemplated DNAse inhibitors include DNAse antibodies.

Most typically, the DNAse inhibitors will be included in quantities that substantially completely preserve the DNA during RNA isolation and/or storage. For example, DNAse inhibitors will be included in the collection container, sample, or fluid such that at least 80%, or at least 85%, or at least 90%, or at least 95%, or at least 98% of the exogenous DNA remains un-degraded (e.g., as measured by gel electrophoresis). Moreover, it should be noted that the DNAse inhibitors can be one type of DNAse inhibitor or multiple types. Use of different DNAse inhibitors can, for example, target distinct DNAses such as DNAseI and DNAse II, as well as other (site specific) exo- and endonucleases.

Moreover, as will be readily appreciated, the (typically biological) fluid may also contain one or more RNAse inhibitors. There are numerous RNAse inhibitors known in the art and/or commercially available, and all of them are deemed suitable for use herein (e.g., mammalian RI, Riboguard, etc.). Additionally contemplated RNAse inhibitors include guanidine thiocyanate and other guanidine salts, cylindrospermopsin, ribonucleoside-vanadyl complexes, recombinant RNasin, RNAse antibodies. Once more, use of different inhibitors advantageously allows targeting different RNAses, including RNAse A, RNAse B, RNAse C, S1 nuclease, RNAse T1, and RNAse H.

Most typically, RNAse inhibitors will be included in quantities that will substantially completely preserve the RNA during RNA isolation and/or storage. For example, RNAse inhibitors will be included in the collection container, sample, or fluid such that at least 90%, or at least 95%, or at least 97%, or at least 98%, or at least 99% of the cfRNA remains un-degraded (as measured by gel electrophoresis of RNA or corresponding cDNA prepared from cfRNA). Of course, it should also be appreciated that the sample, collection container, and/or fluid containing the cfRNA may contain both the RNAse inhibitor and DNAse inhibitor, alone or in combination with the exogenous DNA. Where RNAse inhibitor and DNAse inhibitor are used, it is preferred that the inhibitors are distinct.

Consequently, it should be noted that RNA may be protected (and with that yield in isolation increased) by using any combination or sub-combination of exogenous and/or endogenous DNA, RNAse inhibitor(s), and DNAse inhibitor(s). Moreover, in at least some instances, RNAse or DNAse inhibitors may already be present in an existing formulation (e.g., Cell-Free RNA BCT tubes for RNA isolation and Cell-Free DNA BCT for RNA isolation, commercially available from Streck, 7002 S. 109th Street, Omaha, NE 68128), and it is contemplated that the RNAse or DNAse inhibitors may be combined, and/or supplemented with exogenous DNA to so increase yield of RNA isolation.

In yet further contemplated aspects, the RNA stabilization reagents will not lead to a substantial increase (e.g., increase in total RNA no more than 10%, or no more than 5%, or no more than 2%, or no more than 1%) in RNA quantities in serum or plasma after the reagents are combined with blood. Of course, it should be recognized that numerous other collection modalities are also deemed appropriate, and that the ctRNA and/or ctDNA can be at least partially purified or adsorbed to a solid phase to so increase stability prior to further processing.

Most typically, suitable tissue sources for RNA analysis (and particularly cfRNA) will include whole blood, which is preferably provided as plasma or serum. Alternatively, it should be noted that various other bodily fluids are also deemed appropriate so long as cfRNA is present in such fluids. Appropriate fluids include saliva, ascites fluid, spinal fluid, urine, etc., which may be fresh or preserved/frozen.

Collection of blood or other biological fluids can be performed in numerous manners and will typically include a step of removing particulate matter and cells as is well known in the art. Most typically, but not necessarily, the exogenous DNA (and optionally the DNAse and/or RNAse inhibitors) can be added to the blood collection tubes as an integral component before blood or other bodily fluids are collected. Alternatively, or additionally, the exogenous DNA (and optionally the DNAse and/or RNAse inhibitors) can also be added to the blood collection tubes after the blood or other biological fluid has been collected.

As will be readily appreciated, fractionation of plasma and extraction of cfRNA can be done in numerous manners, however, low-speed/low-g-force protocols are particularly preferred to maintain physical integrity of the cells (which avoids contamination with cellular RNA). In one exemplary preferred aspect, whole blood in 10 mL tubes is centrifuged to fractionate plasma at 1,600 rcf for 20 minutes. The so obtained plasma is then separated and centrifuged at 16,000 rcf for 10 minutes to remove cell debris. Of course, various alternative centrifugal protocols are also deemed suitable so long as the centrifugation will not lead to substantial cell lysis (e.g., lysis of no more than 1%, or no more than 0.1%, or no more than 0.01%, or no more than 0.001% of all cells).

The so prepared mixed nucleic acid solution can then be subjected to various isolation procedures known in the art. For example, where a modified silica resin is used (such as is known from spin columns), the cfRNA and DNA will bind to the resin and can be eluted form the resin at a salt concentration using elution buffers that have insufficient ionic strength to release the DNA form the resin. Alternatively, the silica resins may also operate as a size exclusion separation medium to allow binding and passage (upon elution conditions) of the RNA through the media while retaining the DNA at the top of the medium. Binding and selective elution of DNA and RNA can also be achieved using anion exchange resins (e.g., using commercially available DEAE (diethylaminoethyl) anion exchange resins). Where desired, elution of the cfRNA can performed iteratively such that the eluate of the first elution is used as elution solution of a subsequent elution. Thusly prepared cfRNA can be stored at −80° C. or reverse-transcribed to cDNA and then stored at −4° C. In further contemplated aspects, exogenous DNA may also be added to purified RNA, and especially purified cfRNA, to increase storage stability of the RNA. Preferably, the sequence of the added DNA will not interfere with downstream analyses of the RNA. Thus, non-human DNA is especially preferred as a stabilizer for storage of RNA.

EXAMPLES

The following examples are provided to illustrate various aspects of the inventive subject matter and should not be construed as limiting the invention. For example, for the analyses contemplated herein, specimens are accepted as 10 ml of whole blood drawn into cell-free RNA BCT® tubes RNA stabilizers as further discussed in more detail below. Advantageously, cfRNA is stable in whole blood in the cell-free RNA BCT tubes for seven days while ctDNA is stable in whole blood in the cell-free DNA BCT Tubes for fourteen days, allowing time for shipping of patient samples from world-wide locations without the degradation of cfRNA. Moreover, it is generally preferred that the cfRNA is isolated using RNA stabilization agents that will not or substantially not (e.g., equal or less than 1%, or equal or less than 0.1%, or equal or less than 0.01%, or equal or less than 0.001%) lyse blood cells. In addition, the tubes contain between 10 micrograms and 100 mg exogenous DNA (e.g., ultrapure RNAse free salmon sperm DNA or human DNA as discussed below).

Example 1

Whole blood is obtained by venipuncture and 10 ml is collected into cell-free RNA BCT® tubes (Streck Inc., 7002 S. 109$^{th}$ St., La Vista NE 68128) containing RNA stabilizers. To these tubes is added exogenous DNA, typically between 1-100 micrograms, isolated from the same individual using commercially available DNA isolation kits (e.g., QIAamp DNA Mini Kit). Exogenous DNA is typically present in the elution buffer of the isolation kit or otherwise resuspended in suitable buffer. Optionally, DNaseI inhibitor from Nicotiana tabacum, Calf spleen inhibitor protein, or actin are added to the tubes as DNaseI inhibitor, typically at a concentration of between 10-1,000 microgram/ml. Blood can be stored at 4° C. for up to a week.

Example 2

Cell-free RNA BCT® tubes (Streck Inc., 7002 S. 109$^{th}$ St., La Vista NE 68128) containing RNA stabilizers are modified before use by adding exogenous DNA, typically between 1-100 micrograms, isolated from the same individual using commercially available DNA isolation kits (e.g., QIAamp DNA Mini Kit). DNA is typically present in the elution buffer of the isolation kit or otherwise resuspended in suitable buffer. Whole blood is obtained by venipuncture and 10 ml is collected into the modified cell-free RNA BCT® tubes (Streck Inc., 7002 S. 109$^{th}$ St., La Vista NE 68128) containing RNA stabilizers. Optionally, DNaseI inhibitor from Nicotiana tabacum, Calf spleen inhibitor protein, or actin are added to the tubes as DNaseI inhibitor, typically at a concentration of between 10-1,000 microgram/ml. Blood can be stored at 4° C. for up to a week.

Example 3

Whole blood is obtained by venipuncture and 10 ml is collected into cell-free RNA BCT® tubes (Streck Inc., 7002 S. 109$^{th}$ St., La Vista NE 68128) containing RNA stabilizers. To these tubes is added RNAse free salmon sperm DNA, typically between 1-100 micrograms, as exogenous DNA (commercially available from ThermoFisher, USA). Exogenous salmon sperm DNA is typically present in distilled deionized water or otherwise resuspended in suitable buffer. Optionally, DNaseI inhibitor from Nicotiana tabacum, Calf spleen inhibitor protein, or actin are added to the tubes as DNaseI inhibitor, typically at a concentration of between 10-1,000 microgram/ml. Blood can be stored at 4° C. for up to a week.

Example 4

Cell-free RNA BCT® tubes (Streck Inc., 7002 S. 109$^{th}$ St., La Vista NE 68128) containing RNA stabilizers are modified before use by adding between 1-100 micrograms exogenous DNA, typically between 1-100 micrograms, RNAse free salmon sperm DNA (commercially available from ThermoFisher, USA). Exogenous salmon sperm DNA is typically present in distilled deionized water or otherwise resuspended in suitable buffer. Whole blood is obtained by venipuncture and 10 ml is collected into the modified cell-free RNA BCT® tubes (Streck Inc., 7002 S. 109$^{th}$ St., La Vista NE 68128) containing RNA stabilizers. Optionally, DNaseI inhibitor from Nicotiana tabacum, Calf spleen inhibitor protein, or actin are added to the tubes as DNaseI inhibitor, typically at a concentration of between 10-1,000 microgram/ml. Blood can be stored at 4° C. for up to a week.

Example 5

Whole blood is obtained by venipuncture and 10 ml is collected into cell-free RNA BCT® tubes (Streck Inc., 7002 S. 109$^{th}$ St., La Vista NE 68128) containing RNA stabilizers. To these tubes is added DNaseI inhibitor from Nicotiana tabacum, Calf spleen inhibitor protein, or actin are added to the tubes as DNaseI inhibitor, typically to a final concentration of between 10-1,000 microgram/ml. Optionally, exogenous DNA is added as described in Examples 1-4. Blood can be stored at 4° C. for up to a week.

Example 6

Cell-free RNA BCT® tubes (Streck Inc., 7002 S. 109$^{th}$ St., La Vista NE 68128) containing RNA stabilizers are modified before use by adding DNaseI inhibitor from Nicotiana tabacum, Calf spleen inhibitor protein, or actin to the tubes as DNaseI inhibitor to a final concentration of between 10-1,000 microgram/ml. Whole blood is obtained by venipuncture and 10 ml is collected into the modified cell-free RNA BCT® tubes (Streck Inc., 7002 S. 109th St., La Vista NE 68128) containing RNA stabilizers. Optionally, exogenous DNA is added as described in Examples 1-4. Blood can be stored at 4° C. for up to a week.

Example 7

The sample tubes of Examples 1-6 are centrifuged at 1,600 rcf for 20 minutes, plasma is withdrawn and further centrifuged at 16,000 rcf for 10 minutes to remove cell debris. Plasma is used to isolate cfRNA using commercially available RNA isolation kits following the manufacturer's protocol with slight modification (e.g., QIAamp® Circulating Nucleic Acid Kit) without prior or on column DNAse digestion. RNA is eluted once or twice by reapplication of the first eluate.

Example 8

Yield of cfRNA isolated from tests in Example 7 compared with yield of cfRNA isolated with the RNeasy kit will be between about 5-10%, or between 10-20% higher as achieved with the RNeasy kit. Additionally, integrity (i.e., average RNA degradation) of the RNA isolated using exogenous DNA and/or DNAse inhibitors will be significantly higher than achieved with the RNeasy kit. Where desired, exogenous DNA may be added back to the isolated RNA.

Example 9

So isolated RNA is reverse-transcribed to cDNA using the VILO reverse transcriptase kit (Life Technologies) and random hexamer primers, followed by binding of random hexamers at room temperature for 10 minutes, extension at 42° C. for 60 minutes, heat killing of enzyme at 85° C. for 15 minutes. Resulting cDNA is purified using ZYMO ssDNA and RNA cleanup columns per manufacturer's instructions. PCR of cDNA using beta-actin primer/probes is used to determine relative amount of RNA. QUBIT reading of RNA concentrations will give appearance of no RNA. Resulting cDNA will be PCR amplified with primer/probes developed to amplify RNA sequences rather than DNA by spanning introns when possible.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of collecting cfRNA in blood, the method comprising introducing the blood into a collection tube that contains, before or after the introduction of the blood, at least one of (a) exogenous DNA in an amount of between 1-100 micrograms per 10 mL of blood and (b) a DNaseI inhibitor at a concentration of 10-1,000 microgram/ml, and wherein the exogenous DNA is human DNA or salmon sperm DNA, comprising removing cells from the blood, contacting a solid carrier with the cfRNA and exogenous DNA to adsorb the cfRNA onto the solid carrier, and eluting the cfRNA from the carrier under conditions that separates the eluted RNA from exogenous DNA.

2. The method of claim 1, wherein the exogenous DNA is from the same human as the cfRNA.

3. The method of claim 1, wherein the collection tube further contains a DNAse inhibitor.

4. The method of claim 1, further comprising adding to the collection tube a DNAse inhibitor.

5. The method of claim 1, wherein the collection tube further contains an RNase inhibitor, and optionally a DNAse inhibitor.

6. The method of claim 1, further comprising adding to the collection tube an RNase inhibitor, and optionally a DNAse inhibitor.

7. The method of claim 1, wherein the exogenous DNA has a sequence portion that has sequence homology or sequence complementarity of at least 70% with the cfRNA.

8. The method of claim 1, wherein the exogenous DNA is present in an at least 10-fold molar excess relative to the cfRNA.

9. The method of claim 1, further comprising storing the collected blood at 4° C. for up to a week.

10. The method of claim 1, further comprising eluting the cfRNA without prior or on-carrier DNAse digestion.

11. The method of claim 1, wherein eluting the cfRNA is performed by reapplication of the eluate from the carrier.

12. The method of claim 1, further comprising reverse-transcribing the cfRNA to cDNA.

\* \* \* \* \*